(12) United States Patent
Colman et al.

(10) Patent No.: US 7,074,838 B2
(45) Date of Patent: Jul. 11, 2006

(54) PROCESS FOR THE CATALYTIC OXIDATION OF HYDROCARBONS

(75) Inventors: Derek Alan Colman, Fleet (GB); Trevor John Hesketh, Weybridge (GB); Ian Allan Beattie Reid, Southfields (GB); William Terence Woodfin, North Waltham (GB)

(73) Assignee: Innovene Europe Limited, Middlesex (GB)

( * ) Notice: Subject to any disclaimer, the term of this patent is extended or adjusted under 35 U.S.C. 154(b) by 0 days.

(21) Appl. No.: 11/044,299

(22) Filed: Jan. 28, 2005

(65) Prior Publication Data

US 2005/0137271 A1    Jun. 23, 2005

Related U.S. Application Data

(62) Division of application No. 10/275,343, filed as application No. PCT/GB01/01898 on Apr. 20, 2001, now Pat. No. 6,881,874.

(30) Foreign Application Priority Data

May 3, 2000  (GB)  .................................... 0010693

(51) Int. Cl.
*C07C 27/00*  (2006.01)
*C07C 1/02*  (2006.01)
*C01B 3/26*  (2006.01)

(52) U.S. Cl. ...................... 518/702; 518/703; 252/373; 423/651

(58) Field of Classification Search ................ 518/702, 518/703; 252/373; 423/651
See application file for complete search history.

(56) References Cited

U.S. PATENT DOCUMENTS

| 2,655,442 A | 10/1953 | Mayland | 48/127.9 |
| 4,044,068 A | 8/1977 | Kurtz | |
| 4,376,225 A | 3/1983 | Vora | |
| 5,436,383 A | 7/1995 | Le Peltier et al. | |

FOREIGN PATENT DOCUMENTS

| WO | WO 82/02548 | 8/1982 |
| WO | WO 94/04632 | 3/1994 |
| WO | WO 00/14035 | 3/2000 |

*Primary Examiner*—J. Parsa
(74) *Attorney, Agent, or Firm*—Nixon & Vanderhye

(57) ABSTRACT

Process for the oxidation of a hydrocarbon comprising partially oxidizing in a reaction zone, a mixture comprising a hydrocarbon and an oxygen-containing gas in the presence of a catalyst which is capable of supporting oxidation of the hydrocarbon. Prior to the partial oxidation, the mixture comprising the hydrocarbon and the oxygen-containing gas is passed through a heat exchanger which provides a pressure drop which acts to even the velocity profile and ensure that the reactants flow uniformly over the catalyst.

24 Claims, 1 Drawing Sheet

US 7,074,838 B2

PROCESS FOR THE CATALYTIC OXIDATION OF HYDROCARBONS

This appiication is a divisional of application Ser. No. 10/275,343, filed Jan. 9, 2003 now U.S. Pat. No. 6,881,874, which is a 371 of PCT/GB01/01898, filed Apr. 20, 2001, the contents of which are hereby incorporated by reference in this application.

The present invention relates, in general, to the cataytic oxidation of hydrocarbons and, in particular, to the catalytic oxidative dehydrogenation of hydrocarbons to produce olefins.

BACKGROUND OF THE INVENTION

Processes for the catalytic oxidation of hydrocarbons are well known, for example, the oxidation of methane to produce syngas; the oxidation of ethylene to produce ethylene oxide; the oxidation of ethylene and acetic acid to produce vinyl acetate; the production of maleic anhydride from the oxidation of butene, butane or benzene; the production of phthalic anhydride by the oxidation of naphthalene or o-xylene; the ammoxidation of propane to acrylonitrile.

The catalytic oxidative dehydrogenation of hydrocarbons is a known process for the production of olefins. An example of such a process is described in EP-A-0 332 289. In this process, a hydrocarbon and an oxygen-containing gas are contacted with a catalyst, which is capable of supporting combustion beyond the fuel rich limit of flammability. The hydrocarbon is partially combusted, and the heat produced is used to drive the dehydrogenation of the hydrocarbon feed into olefins. Optionally, a hydrogen co-feed is also burned, and the heat produced by this combustion reaction is used to drive the dehydrogenation of the hydrocarbon.

Generally, in a catalytic oxidative dehydrogenation process, the reactants (hydrocarbon and an oxygen-containing gas) are passed over the catalyst directly to produce olefin product. Typically, the hydrocarbon is a saturated hydrocarbon such as a $C_2$–$C_{10}$ saturated hydrocarbon, such as ethane or a mixture of saturated hydrocarbons such as a mixture of $C_2$–$C_{10}$ hydrocarbons, naphtha or gas oil. The hydrocarbon may be gaseous or liquid at ambient temperature and pressure but is typically gaseous.

It is desirable in processes for the catalytic oxidation of hydrocarbons to have effective mixing of the reactants and/or uniform velocity profile of the reactant mixture prior to contact with the catalyst. However, although the reactants (hydrocarbon and oxygen-containing gas) may be pre-mixed prior to being introduced into the reactor, the velocity profile of the reactant mixture is often still non-uniform. Such a non-uniform velocity profile can lead to an unstable reaction. For example, high velocity gas mixtures over only part of the catalyst can lead to a decrease in selectivity. Where the oxidation reaction is one which is carried out close to its flammable limit, such as in the catalytic oxidative dehydrogenation of hydrocarbons, low velocity gas mixtures over only part of the catalyst can result in flash-backs.

Moreover, the heat generated by the oxidation reaction is generally not distributed evenly, reducing the efficiency of the oxidation process and resulting in potential loss of product.

BRIEF DESCRIPTION OF THE INVENTION

We have now found that the above disadvantages may be alleviated by passing the reactants (hydrocarbon and an oxygen-containing gas) through a heat exchanger prior to contacting the reactants with the catalyst.

Accordingly, the present invention provides a process for the oxidation of a hydrocarbon said process comprising:

partially oxidising in a reaction zone, a mixture comprising a hydrocarbon and an oxygen-containing gas in the presence of a catalyst which is capable of supporting oxidation of the hydrocarbon, wherein prior to said partial oxidation, said mixture comprising the hydrocarbon and the oxygen-containing gas is passed through a heat exchanger.

The heat exchanger employed in the present process provides a pressure drop, which acts to even the velocity profile of the reactant mixture. This ensures that the reactants subsequently flow uniformly over the catalyst, improving the efficiency of the oxidation reaction.

Suitable heat exchangers include, but are not limited to, shell and tube or plate fin heat exchangers. The velocity profile of the reactant mixture will generally be dependent on the distance between adjacent gas outlets of the heat exchanger. Thus, an improved reactant mixture velocity profile may be achieved by minimising the distance between adjacent gas outlets. Suitably, the adjacent gas outlets may be several millimetres apart, for example in the range 1 to 10 mm, preferably, 1 to 5 mm, especially 2 to 5 mm.

In a preferred embodiment of the present invention the, heat exchanger is a compact heat exchanger. Compact heat exchangers generally comprise a plurality of channels, which ensure that fluid (gas or liquid) entering the channels develops fully into a substantially uniform velocity profile within a relatively short distance of exiting the channel outlets. Preferably, the fluid develops fully into a substantially uniform velocity profile within a distance of less than 100 mm from exiting the channel outlets. More preferably, a substantially uniform velocity profile may be achieved within a distance of less than 60 mm, even more preferably, less than 40 mm, and most preferably, less than 25 mm and especially less than 15 mm from exiting the channel outlets.

The compact heat exchanger may be made by diffusion bonding a plurality of metal plates together to form a stack. Grooves may be etched or otherwise formed into the surface of each plate, such that the resulting structure defines a plurality of channels. Preferably, the channels of the compact heat exchanger are parallel to one another. The channels may be of any suitable shape such as linear or z-shaped. The cross-section of each channel may be any suitable shape. Preferably, each channel is of the same shape. Preferably, each channel is semi-circular. Where the channels are semi-circular, the radius of each channel may measure 0.1 to 2.5 mm, preferably 0.25 to 1.5 mm, and most preferably, 0.5 to 1 mm.

The compact heat exchanger may be any suitable shape in cross section, for example, circular, rectangular or square. Preferably, the compact heat exchanger is square in cross section. Where a compact heat exchanger of square cross section is employed, each side of the square may be in the range 100 to 3000 mm, preferably, in the range 400 and 2000 mm, more preferably, in the range 1200 and 1800 mm. Similarly, where a circular compact heat exchanger is employed, the diameter of the exchanger may be in the range 100 to 3000 mm, preferably, in the range 400 and 2000 mm, more preferably, in the range 1200 and 1800 mm.

The reactant mixture may be preheated and, preferably, is preheated, prior to entry into the reaction zone. Generally, the reactant mixture is preheated to temperatures below the autoignition temperature of the reactant mixture. Typically, in the catalytic oxidative dehydrogenation of hydrocarbons, preheat temperatures of up to 200° C. but below the autoigiltion temperature of the reactants are employed. Preferably, the heat exchanger preheats the reactant mixture to a temperature of up to 30° C. below the autoignition temperature of the mixture.

Advantageously, the use of the heat exchanger may allow the reactant mixture to be heated to high preheat temperatures such as temperatures at or above the autoignition temperature of the reactant mixture. The benefits of using preheat temperatures above the autoignition temperature of the reactant mixture will vary depending on the particular catalytic oxidation process employed. Where the process is the catalytic oxidative dehydrogenation of hydrocarbon to produce olefin, the use of high pre-heat temperatures is beneficial in that less oxygen reactant is required which leads to economic savings. In addition, in the catalytic oxidative dehydrogenation of hydrocarbon to produce olefin, the use of high preheat temperatures can result in improved selectivity to olefin product. It should be understood that the autoignition temperature of a reactant mixture is dependent on pressure as well as the feed composition: it is not an absolute value. Typically, in the catalytic oxidative dehydrogenation of hydrocarbon to produce olefin, where the hydrocarbon feed is ethane at a pressure of 2 atmospheres, a preheat temperature of up to 450° C. may be used.

It should be understood that the residence time of the reactant mixture in the heat exchanger will be dependent upon a number of factors such as the length of the heat exchanger tubes and the velocity of the reactant mixture through the heat exchanger. However, where the reactant mixture is heated to above its autoignition temperature premature reaction of the reactants may occur. To avoid such premature reaction the heat exchanger should preferably provide a residence time of the reactant mixture which is less than the ignition delay time for the temperature of the reactant mixture. Typically, the residence time may be in the range 10 to 1000 milliseconds, preferably 10 to 100 milliseconds.

In use, the heat exchanger employed in the present invention may be heated by any suitable means. Suitably, the heat exchanger may be indirectly heated by the heat generated by the partial combustion of the reactants. It may also be possible to supplement the heat generated by the partial oxidation reaction by heating the heat exchanger by external means. For example, the whole or part of the heat exchanger may be heated electrically. Alternatively or additionally, a hot fluid, such as steam, may be passed through the heat exchanger. In certain circumstances, for example to prevent flashback into the heat exchanger, it may be desirable to cool the whole or part of the heat exchanger. This may be achieved by passing a cooling fluid such as cooling water through the exchanger.

Although the hydrocarbon and oxygen-containing gas may be pre-mixed prior to being introduced into a reaction zone, the extent of mixing of the gaseous reactants is often still uneven. Such uneven mixing of the reactants can lead to an unstable reaction.

Advantageously, improved mixing and/or improved velocity profile of the reactants may be achieved by passing the reactant mixture through a baffle zone prior to entry into the heat exchanger.

Thus, in another aspect of the invention, the hydrocarbon and oxygen-containing gas are mixed in at least one baffle zone, prior to being passed through the heat exchanger. The baffle zone is defined by a housing, which contains at least one baffle plate. By baffle plate is meant any device which serves to correct the flow of reactants thereby improving mixing and/or velocity profile of the reactants.

The housing may be any suitable shape in cross-section, for example, square, rectangular or circular. A housing having a square cross section is preferred. Most preferably, the housing defines a cubic baffle zone. To minimise the volume of the reactant mixture in the housing, it is preferable to minimise the volume of the baffle zone housing.

The housing may be of any suitable material such as metal.

Suitably, the baffle plate may be solid (non-perforated). Preferably, the baffle plate is of circular cross section. The baffle plate may be of any suitable material such as metal.

Preferably, the baffle plate is disposed substantially at a right angle to the direction of flow of the reactant mixture entering the baffle zone. Such orientation of the plate promotes mixing of the reactants. It has been found that where the angle of the plate deviates slightly from the perpendicular, for example, by a few degrees, the extent of mixing is inferior to that obtained when the plate is perpendicular to the flow of reactants.

Preferably, the baffle plate is located substantially midway along the length of the housing such that the distance from the outlet of the mixing device to the plate is approximately equal to the distance from the plate to the inlets of the heat exchanger channels.

Suitably, where the baffle plate is circular and the housing is of square cross section, the ratio of the length of the housing to the diameter of the baffle plate is in the range 4:1 to 1:1, such as 2:1.

The hydrocarbon and oxygen-containing gas reactants are pre-mixed prior to introduction into the baffle zone. Pre-mixing of the reactants may be carried out by any suitable means. Suitable mixing means include devices which are capable of causing substantial mixing of the reactants prior to entry into the baffle zone such as one or more injectors, for example, gas injectors. Preferred mixing devices are those which provide for mixing of at least 80% of the reactants prior to entry into the baffle zone.

Suitably, the hydrocarbon is entrained in the oxygen-containing gas prior to entry into the baffle zone. Preferably, the oxygen-containing gas is injected into the baffle zone by one or more gas injectors. Suitably, the gas injector may be located within a tube or other housing such that the oxygen-containing gas stream can be entrained with a hydrocarbon stream entering the tube or housing. The injector may have a flared section around the injector nozzle so as to provide a constriction in the tube. The hydrocarbon is fed over the flared section at lower velocity than the velocity of the oxygen-containing gas. The difference in velocities, and the shear between the oxygen containing gas and hydrocarbon streams causes the hydrocarbon to become entrained in the oxygen-containing gas. Preferably, the velocity ratio of the oxygen-containing gas to hydrocarbon is 20:1 to 2:1, more preferably, 3:1 to 8:1. The relative velocities of the reactants and the distance they have to travel before reaching the baffle zone should be carefully calculated and monitored, to ensure that the reactants are sufficiently dispersed as they leave the exit port of the injector and enter the baffle zone.

The reactant mixture entering the baffle zone impinges the baffle plate and is deflected by the baffle plate thereby reducing the momentum of the mixture. This reduction in momentum provides a more uniform velocity and pressure profile of the mixture prior to entry into the heat exchanger. The reduction in momentum is enhanced when the baffle plate is positioned in-line with the outlet of the mixing device (such as the exit port of an injector nozzle), that is, the outlet of the mixing device is disposed substantially perpendicular to the baffle plate.

Preferably, the dimensions of the baffle plate are such that substantially all of the reactants impinge on the baffle plate. The ratio of the diameter of a circular baffle plate to the diameter of the outlet of the mixing device is preferably, 1–5:1, more preferably, 1–3:1, and most preferably, 2:1.

A plurality of baffle zones may be employed in the process of the present invention. Each baffle zone housing may be fed with a single mixing device or a plurality of mixing devices, preferably a plurality of mixing devices. Preferably, where a plurality of mixing devices feeds a single baffle zone housing the ratio of baffle plates to mixing devices is 1:1. However, a baffle zone housing fed by a plurality of mixing devices may house a single baffle plate.

Preferably, to ensure that the flow rates of reactants through the mixing devices are uniform, the outlet of each mixing device has substantially the same diameter.

Alternatively, the baffle zone may comprise a housing without a baffle plate. In this instance, the hydrocarbon/oxygen-containing gas mixture may be fed substantially tangentially into the housing using one or more mixing devices.

Optionally, the hydrocarbon and/or oxygen-containing gas may be preheated before being introduced into the baffle zone. The temperature to which the reactants may be preheated, however, is limited by the autoignition temperature of the feed.

Once the reactant mixture has passed through the baffle zone and the heat exchanger, it is contacted with a catalyst which is capable of supporting oxidation of the hydrocarbon.

The catalyst which is used in the oxidation reaction of the present invention will depend on the specific oxidation process to be employed. For example, where the oxidation process is the oxidation of methane to produce syngas suitable catalysts include platinum/rhodium or nickel based catalysts. Suitable catalysts for the oxidation of ethylene to produce ethylene oxide include silver based catalysts. In the oxidation of ethylene and acetic acid to produce vinyl acetate suitable catalysts include palladium based catalysts such as palladium/gold catalysts. Suitable catalysts for the production of maleic anhydride from the oxidation of butene, butane or benzene include vanadium and/or molybdenum based catalysts. Typically, in the production of phthalic anhydride by the oxidation of naphthalene or o-xylene vanadium based catalysts are employed. Suitable catalysts in the ammuoxidation of propane to acrylonitrile include bismuth based catalysts. These and other suitable catalysts for the afore-mentioned and other hydrocarbon oxidation reactions are known in the art.

Preferably, the oxidation reaction is carried out in a fixed bed reactor.

Any suitable hydrocarbon may be employed, for example, $C_1$ to $C_6$ hydrocarbons, such as, $C_1$ to $C_6$ alkanes, or $C_2$ to $C_6$ olefins. The $C_1$ to $C_6$ hydrocarbon may be linear, branched or cyclic. Aromatic hydrocarbons such as benzene and naphthalene may also be employed.

Any suitable oxygen-containing gas may be employed, for example molecular oxygen or air.

Suitably, the oxidation reaction of the present invention is any hydrocarbon oxidation reaction which may be carried out in a fixed bed reactor. Suitably, the oxidation reaction reaction may be the oxidation of ethylene to ethylene oxide, the oxidation of ethylene and acetic acid to vinyl acetate, the oxidation of napthalene to phthalic anhydride, the oxidation of ortho-xylene to phthalic anhydride, the ammoxidation of propane to acrylonitrile, the oxidation of gaseous paraffinic hydrocarbons, such as methane, to syngas, the oxidation of $C_4$ hydrocarbon, such as butane and/or butene to maleic anhydride and the oxidation of benzene to maleic anhydride.

The oxidation reaction conditions such as temperature and pressure will depend on the specific oxidation reaction employed. Suitable reaction conditions are known in the art.

In a preferred embodiment of the present invention there is provided a process for the catalytic oxidative dehydrogenation of hydrocarbons to produce olefins such as ethylene.

Accordingly, the present invention provides a process for the production of an olefin said process comprising:
   partially combusting in a reaction zone, a mixture of a hydrocarbon and an oxygen-containing gas in the presence of a catalyst which is capable of supporting combustion beyond the fuel rich limit of flammability to produce the olefin, wherein prior to said partial combustion, said mixture of the hydrocarbon and the oxygen-containing gas is passed through a heat exchanger.

The process comprises contacting a hydrocarbon or a mixture of hydrocarbons and an oxygen-containing gas with a catalyst under catalytic oxidative dehydrogenation reaction conditions to produce the olefin.

The hydrocarbon may be any hydrocarbon which can be converted to an olefin, preferably a mono-olefin, under the catalytic oxidative dehydrogenation reaction conditions employed.

The process of the present invention may be used to convert both liquid and gaseous hydrocarbons into olefins. Suitable liquid hydrocarbons include naphtha and gas oils. Preferably, however, gaseous hydrocarbons such as ethane, propane, butane and mixtures thereof are employed.

Any suitable oxygen-containing gas may be employed, for example molecular oxygen, air or molecular oxygen diluted with an unreactive gas such as nitrogen, argon, carbon dioxide or helium.

Any molar ratio of hydrocarbon to oxygen is suitable provided the desired olefin is produced in the process of the present invention. The preferred stoichiometric ratio of hydrocarbon to oxygen is 5 to 16, preferably, 5 to 13.5 times, preferably, 6 to 10 times the stoichiometric ratio of hydrocarbon to oxygen required for complete combustion of the hydrocarbon to carbon dioxide and water.

The hydrocarbon is passed over the catalyst at a gas hourly space velocity of greater than 10,000 $h^{-1}$, preferably above 20,000 $h^{-1}$ and most preferably, greater than 100,000 $h^{-1}$. It will be understood, however, that the optimum gas hourly space velocity will depend upon the pressure and nature of the feed composition.

Advantageously, the hydrocarbon may be pre-heated. The temperature to which the hydrocarbon, oxygen-containing gas and (optionally) hydrogen mixture may be preheated, however, is limited by the autoignition temperature of the feed. Preferably, hydrogen is co-fed with the hydrocarbon and molecular oxygen-containing gas into the reaction zone. The molar ratio of hydrogen to oxygen can vary over any operable range provided that the desired olefin product is produced. Suitably, the molar ratio of hydrogen to oxygen is in the range 0.2 to 4, preferably, in the range 0.5 to 3.

In the presence of the catalyst, hydrogen combusts preferentially relative to the hydrocarbon, thereby increasing the olefin selectivity of the overall process.

In addition, the feed may comprise a diluent-such-as nitrogen, carbon monoxide and steam.

The partial combustion reaction may be suitably carried out at a catalyst exit temperature of between 600° C. and 1200° C., preferably between 850° C. and 1050° C. and most preferably, between 900° C. and 1000° C.

The catalytic oxidative dehydrogenation process may be carried out at atmospheric or super atmospheric pressure. Suitably, the pressure may be within the range 0 to 2 bara, preferably, 1.5 to 2 bara, for example, 1.6 to 1.8 bara, especially 1.65 bara. Pressures of, for example, 2 to 50 bara, may also be suitable.

The catalyst employed in the catalytic oxidative dehydrogenation process is one which is capable of supporting combustion beyond the fuel rich limit of flammability. Suitable catalysts may comprise one or more Group VIII transition metals. The Group VIII transition metals include iron, cobalt, nickel, ruthenium, rhodium, palladium, osmium, iridium and platinum. Preferably, the Group VIII transition metal is rhodium and more particularly, platinum and palladium.

Preferably, the Group VIII transition metal is employed in combination with a catalyst promoter. The promoter may be a Group IIIA (aluminium, gallium, indium and thallium), IVA (for example, germanium, tin and lead) and/or VA (for example, arsenic and antimony) metal. Alternatively, the promoter may be a transition metal which is different to the Group VIII transition metal.

Preferred Group IIIA metals include gallium and indium. Preferred Group IVA metals include germanium, tin and lead. Preferred Group VA metals include antimony. Preferred transition metals include those from Groups IB, IIB, VIB, VIIB and VIIIB of the Periodic Table. Examples of suitable transition metals include chromium, molybdenum, tungsten, iron, ruthenium, osmium, cobalt, rhodium, iridium, nickel, platinum, copper, silver, gold, zinc, cadmiun and mercury. Preferred transition metal promoters are molybdenum, rhodium, ruthenium, iridium, platinum, copper and zinc. Suitably, the catalyst may be Pt/Ga, Pt/In, Pt/Sn, Pt/Ge, Pt/Cu, Pd/Sn, Pd/Ge, Pd/Cu, Pd/Sn, Pd/Ge and Rh/Sn. Of these Pt/Cu and Pt/Sn are preferred.

In another embodiment of the present invention, the catalyst comprises platinum and palladium, and a further metal selected from Group IIIA, Group IVA or the transition metal series of the Periodic Table. Suitably, the catalyst may be Pt/Pd/Cu.

For the avoidance of doubt, the Group VIII transition metal and promoter may be present in any form, for example, as the metal or in the form of a metal compound, such as a metal oxide.

Suitable catalytic oxidative dehydrogenation catalysts are described in more detail in EP-A-0 332 289, WO 97/26987, GB 9930598.9 and GB 9930597.1, the contents of which are herein disclosed by reference.

The catalyst employed in the present invention may be unsupported, for example, the catalyst may be in the form of a metal gauze.

Preferably, the catalyst is supported on any suitable support Suitably, the support is a metal or ceramic support, preferably a ceramic support. Suitable ceramic supports include lithium aluminium silicate (LAS), alumina ($\alpha$-$Al_2O_3$), yttria stabilised zirconia, alumina titanate, niascon, and calcium zirconyl phosphate. The support may be wash-coated, for example, with $\gamma$-$Al_2O_3$.

The catalyst may be employed in the form of tiles, preferably, with chamfered edges. Such tiles may be placed adjacent to one another to form a catalyst bed of a desired size. It may be desirable to seal the area between the bed and the reactor walls to avoid unreacted reactants from flowing through the gap between the bed and the reactor. Preferably, an intumescent sealant such as vermiculite base is employed. Alternatively, the sealant may comprise compressed silica-fibre mats.

Where possible, the heat produced by the partial combustion of the hydrocarbon and oxygen-containing gas hydrogen is recycled, for example, to heat the reactants in the heat exchanger.

Where the cracking reaction is carried out at superatmospheric pressure, the reaction products may be quenched, for example, with water, as they emerge from the reaction chamber to avoid further reactions taking place. Quenching may not be necessary for reactions carried out at relatively low pressure, for example, pressures less than 5 bara.

Any coke produced in the process of the present invention may be removed by mechanical means, or by decoking. Suitable decoking methods are described in EP 0-A-709 446.

BRIEF DESCRIPTION OF THE DRAWING

The invention will now be illustrated by way of example only and with reference to FIG. 1 and to the following examples.

DETAILED DESCRIPTION OF PREFERRED EMBODIMENTS

Figure 1:
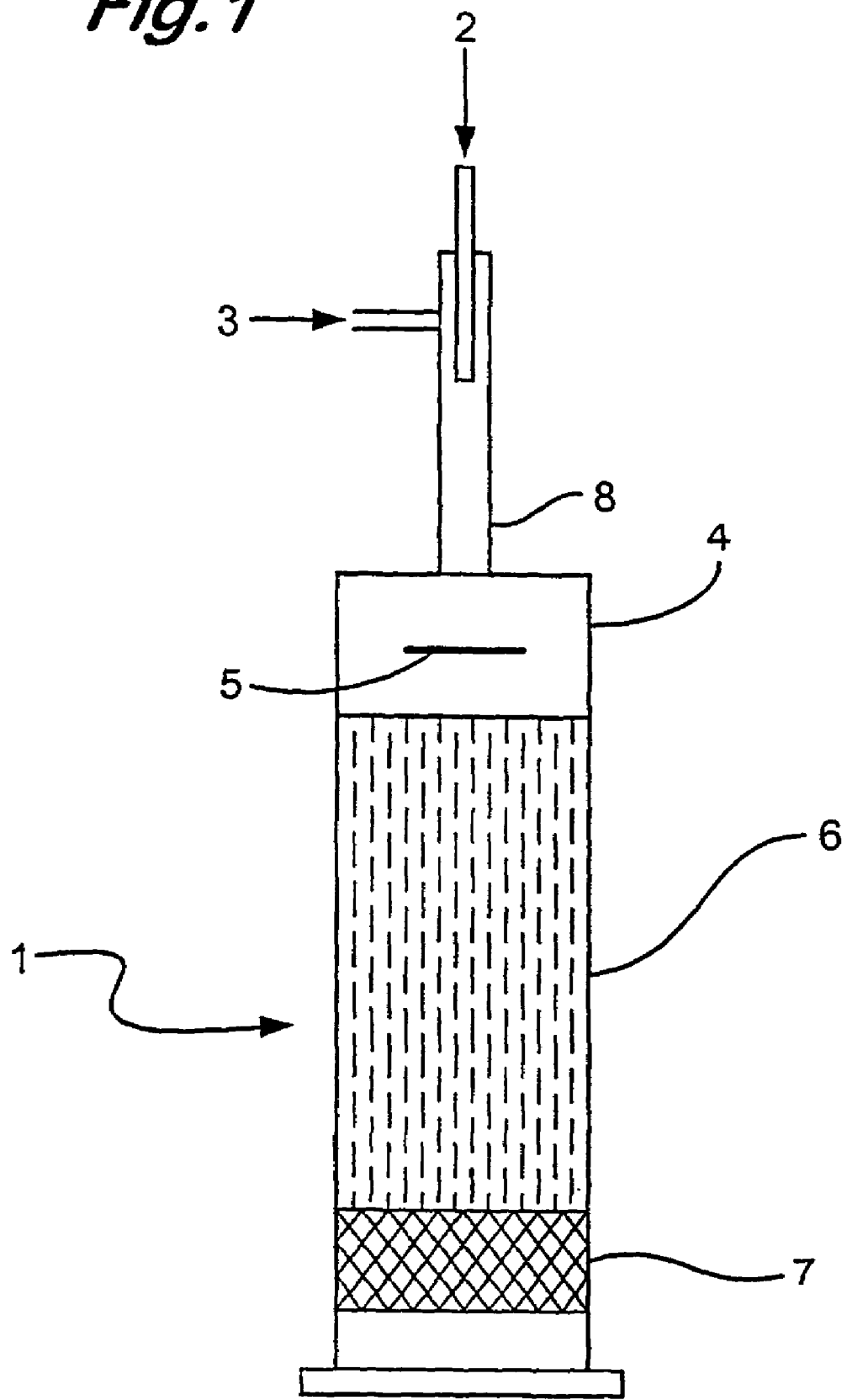
FIG. 1 represents in schematic form, apparatus suitable for use in the process of the present invention.

The apparatus (1) is provided with means for supplying an oxygen-containing gas (2) and a means for supplying a hydrocarbon and optionally hydrogen (3). Depending on the scale of the process there may be a single means or several means for the supply of reactants. The means for supplying an oxygen-containing gas (2) and a means for supplying a hydrocarbon and optionally hydrogen (3) are welded to the baffle zone housing (4).

The apparatus (1) also comprises a baffle zone housing (4) which is provided with a baffle plate (5). The baffle zone housing (4) is cubic and made of stainless steel. The baffle plate (5) is solid (non-perforated) and made of monel. The ratio of the length of the baffle zone housing to the diameter of the baffle plate is 2:1. The baffle plate (5) is disposed substantially perpendicular to the outlet(s) of the reactant supply means and approximately midway along the length of the baffle zone housing (4). The ratio of the diameter of the baffle plate to the diameter of the exit port of the nozzle of the injector (8) is 2:1. Depending on the scale of the process, the baffle zone may comprise either a single baffle zone or several baffle zones. Each baffle zone may comprise a single or several baffle plates.

The baffle zone housing (4) is bolted to a heat exchanger (6).

The apparatus (1) further comprises a compact heat exchanger (6) of square cross-section and having substantially z-shaped channels of semi-circular cross-section and 1 mn in radius. The heat exchanger (6) is bolted to the reactor (7). Suitable compact heat exchangers are manufactured by Heatric Limited. The apparatus (1) also comprises a reactor (7). The cross-sectional shape of the reactor is square, so as to substantially match the cross-sectional shape of the heat exchanger (6). To minimise heat losses, the reactor is insulated both internally and externally.

In use, the reactor (7) is provided with at least one catalyst which is capable of supporting combustion beyond the fuel rich limit of flammability. Suitably, the catalyst is a supported catalyst. The catalyst is placed below an alumina heat shield (not shown). An oxygen-containing gas is fed to the apparatus (1) from a supply (2) suitably via a gas injector (8). A gaseous hydrocarbon feedstock suitably comprising ethane and optionally hydrogen is fed to the apparatus (1) from supply (3) suitably via a gas injector (8). The ratio of the velocity of the oxygen containing gas to the velocity of the hydrocarbon feed is 5:1. The oxygen-containing gas, hydrocarbon and optionally hydrogen mix in the injector (8) to form a reactant mixture prior to exiting the outlet of the injector (8) into baffle zone (4). On entering baffle zone (4) the reactant mixture impinges the baffle plate (5) and is deflected into the channels of the compact heat exchanger (6). The compact heat exchanger (6) is heated by steam. On passage through the channels of the compact heat exchanger (6) the reactant mixture is preheated to the required temperature. On exiting the channels of the compact heat exchanger (6) the reactant mixture passes into reactor (7) whereupon it contacts the catalyst. In the reactor (7) at least a portion of the hydrocarbon feed combusts to produce water and carbon oxides. The hydrogen co-feed, if present, combusts to produce water. Both of these combustion reactions are exothermic and the heat thereby produced is used to drive the dehydrogenation of hydrocarbon to olefin product General Ethane Catalytic Oxidative Dehydrogenation Reaction Method

EXAMPLES

Typically, a platinum-copper catalyst comprising nominal loading of 3 wt % platinum and 1 wt % copper was supported on 99.5% alumina foam (of porosity 45 pores per inch) (Vesuvius Hi-Tech Ceramics Inc) to provide a catalyst bed sized to match the cross sectional area of heat exchanger, 60 mm in depth and a volume of 1008 cm$^3$. The supported catalyst was then loaded into a fixed bed reactor. An alumina heat shield was positioned above the catalyst. The catalyst was heated under nitrogen to 200° C. A flow of nitrogen was maintained immediately below the catalyst to ensure a non-flammable atmosphere until reaction was established on the catalyst.

Flows of ethane, hydrogen and oxygen were then introduced into an apparatus as described for FIG. 1. The flows of ethane, hydrogen and oxygen were gradually increased over a 1 hour period to provide a gas velocity at the upstream catalyst face of 4.35 m/s at the feed temperature with the following feed mass ratios to oxygen:ethane: oxygen 1.84 and hydrogen:oxygen 0.12. During this period the catalyst exit temperature rose steadily and then stabilized at 850° C.

After the 1 hour equilibration period the nitrogen flow was reduced to 0 kg/h over a 2 hour period. The ethane, hydrogen and oxygen flows were adjusted to achieve target flows.

The reactant mixture was heated to the required pre-heat temperature by the compact heat exchanger.

The catalytic oxidative dehydrogenation reaction was carried out at a pressure of 1.8 bara.

The product composition was analysed by gas chromatography. The feed and product flow rates were determined by coriolis type flow meters.

From analysis of the feed and product flow rates and compositions the ethane conversion and selectivity to ethylene was calculated.

The velocity profile and the degree of mixing of the reactants may be determined by techniques such as computational fluid dynamic modelling (CFD modelling) and physical flow models. Alternatively and/or additionally, thermocouples may be located below the catalyst to confirm uniform reaction across the catalyst Uniform reaction will be obtained when the velocity profile and the extent of mixing of the reactant mixture fed to the catalyst is uniform.

Example 1

In this Example, ethane, oxygen and hydrogen were utilised as feed in the general reaction method above. The reactant mixture was pre-heated to a temperature below the autoignition temperature of the mixture. The results are shown in Table 1 below.

Example 2

The data in this Example was obtained by thermochemical analysis of the data in Example 1. The preheat temperature of the reactant mixture was set at a temperature above its autoignition temperature. The results are shown in Table 1 below.

TABLE 1

|  | Example 1 | Example 2 |
| --- | --- | --- |
| Preheat Temperature ° C. | 195 | 450 |
| Ethane:Oxygen ratio | 2.43 | 3.08 |
| Hydrogen:Oxygen ratio | 0.12 | 0.12 |
| Feed velocity at catalyst face at preheat temperature m/s | 5.47 | 7.43 |
| Ethane conversion % | 69.14 | 68.71 |
| Ethylene selectivity (g/100 g C2 converted) | 72.29 | 73.74 |
| Carbon monoxide selectivity (g/100 g C2 converted) | 15.28 | 12.13 |
| Carbon dioxide selectivity (g/100 g C2 converted) | 2.01 | 1.59 |
| Methane selectivity (g/100 g C2 converted) | 8.57 | 8.74 |
| Acetylene selectivity (g/100 g C2 converted) | 0.59 | 0.60 |
| C3 selectivity (g/100 g C2 converted) | 2.16 | 2.19 |
| C4 selectivity (g/100 g C2 converted) | 2.0 | 2.1 |
| C5+ selectivity (g/100 g C2 converted) | 0.38 | 0.38 |

It is expected and believed that in the absence of the heat exchanger and/or baffle zone, the conversion of ethane and/or selectivity to ethylene would be inferior to the results obtained above.

Example 2 demonstrates that the use of a preheat temperature above the autoignition temperature of the reactant mixture results in improved selectivity to olefin product and a reduction in oxygen usage compared to the use of a preheat temperature below the autoignition temperature of the reactant mixture (Example 1).

Example 3

Using the apparatus as described in FIG. 1, the distribution of oxygen in an oxygen/ethane gas mixture (ratio of oxygen to ethane, 1:2.4) fed into the baffle zone (4) by the injector (8), passing through the baffle zone (4) and into the compact heat exchanger (6) was analysed by 3D CFD modelling using Fluent™ software. In this Example the baffle plate (5) was disposed perpendicularly i.e at 90 degrees to the oxygen/ethane gas flow.

The CFD modelling results demonstrated that the oxygen and ethane partially mix in the injector (8) prior to entry into the baffle zone (4). After deflection by the baffle plate (5) the oxygen and ethane gases appear to be substantially mixed (approximately 99% mixed)

No further mixing of the gases was observed after exit from the baffle zone (4).

Example 4

Example 3 was repeated except that the baffle plate (5) was placed at an angle to the oxygen/hydrocarbon gas flow of 2.6 degrees.

The CFD modelling results show that the mixing of the oxygen and ethane gases after deflection by the baffle plate (5) was not as good (approximately 96% mixed) as that obtained in Example 4 (where baffle plate was perpendicular to the gas flow). Examples 3 and 4 clearly demonstrate that the mixing of oxygen and ethane is not complete at the baffle plate. Thus, in the absence of a baffle zone there would be a range of ethane/oxygen gas mixtures contacting the catalyst resulting in a less efficient auto-thermal cracking process.

The CFD modelling also demonstrated that in both Examples 3 and 4 the momentum of the injected reactant mixture was reduced by the baffle plate (5) resulting, in each case, in an improved, that is a more uniform velocity profile of the reactant mixture prior to entry into the heat exchanger (6).

The invention claimed is:

1. A process for the oxidation of a hydrocarbon said process comprising:
partially oxidising in a reaction zone, a mixture comprising a hydrocarbon and an oxygen-containing gas in the presence of a catalyst which is capable of supporting oxidation of the hydrocarbon, wherein prior to said partial oxidation, said mixture comprising the hydrocarbon and the oxygen-containing gas is passed through a heat exchanger, and wherein the heat exchanger provides a pressure drop which acts to even the velocity profile and ensure that the reactants flow uniformly over the catalyst.

2. A process according to claim 1 wherein the heat exchanger has gas outlets and the distance between adjacent gas outlets is in the range 1 to 10 mm.

3. A process according to claim 1 wherein the heat exchanger provides a residence time in the range 10 to 1000 milliseconds.

4. A process according to claim 1 wherein the heat exchanger is a compact heat exchanger.

5. A process according to claim 4 wherein the fluid exiting the channel outlets of the compact heat exchanger develops into a substantially uniform velocity profile within a distance of less than 100 mm from the channel outlets.

6. process according to claim 5 wherein substantially uniform velocity profile is achieved within a distance of less than 25 mm from the channel outlets.

7. A process according to claim 4 wherein the compact heat exchanger has a square cross section.

8. A process according to claim 7 wherein each side of the square is in the range 100 to 3000 mm.

9. A process according to claim 1 wherein the heat exchanger preheats the mixture of the hydrocarbon and oxygen-containing gas to a temperature below the autoignition temperature of the mixture.

10. A process according to claim 1 wherein the heat exchanger preheats the mixture of the hydrocarbon and oxygen-containing gas to a temperature at or above the autoignition temperature of the mixture.

11. A process according to claim 1 wherein the hydrocarbon and oxygen-containing gas are mixed in at least one baffle zone prior to being passed through the heat exchanger.

12. A process according to claim 11 wherein the baffle zone comprises a housing and at least one baffle plate is contained within the housing.

13. A process according to claim 12 wherein the baffle plate is of circular cross section.

14. A process according to claim 12 wherein the baffle plate is disposed substantially perpendicularly to the direction of flow of the hydrocarbon and oxygen-containing gas mixture.

15. A process according to claim 12 wherein the baffle plate is located substantially midway along the length of the housing.

16. A process according to claim 12 wherein the housing defines a cubic baffle zone.

17. A process according to claim 16 wherein the baffle zone is of circular cross section and the ratio of the length of the housing to the diameter of the baffle plate is in the range 4:1 to 1:1.

18. A process according to claim 11 wherein the hydrocarbon and oxygen-containing gas mixture is pre-mixed in at least one mixing device prior to entry into the baffle zone.

19. A process according to claim 18 wherein the baffle zone comprises a circular baffle plate and the ratio of the diameter of the baffle plate to the diameter of the outlet of the mixing device is 1–5:1.

20. A process according to claim 18 wherein a plurality of mixing devices feed a single baffle zone housing which comprises a plurality of baffle plates.

21. A process according to claim 20 wherein the ratio of baffle plates to mixing devices is 1:1.

22. A process according to claim 11 wherein the baffle zone comprises a housing without a baffle plate into which the hydrocarbon/oxygen-containing gas mixture is fed substantially tangentially using one or more mixing devices.

23. A process according to claim 1 wherein the oxidation reaction is selected from the group consisting of the oxidation of ethylene to ethylene oxide, the oxidation of ethylene and acetic acid to vinyl acetate, the oxidation of naphthalene to phthalic anhydride, the oxidation of ortho-xylene to phthalic anhydride, the ammoxidation of propane to acrylonitrile, the oxidation of gaseous paraffinic hydrocarbons to syngas, the oxidation of $C_4$ hydrocarbon to maleic anhydride and the oxidation of benzene to maleic anhydride.

24. A process according to claim 23 wherein the oxidation reaction is the oxidation of methane to produce syngas.

\* \* \* \* \*